(12) United States Patent
Poehlmann-Martins et al.

(10) Patent No.: US 12,064,644 B2
(45) Date of Patent: Aug. 20, 2024

(54) PINHOLE COLLIMATOR SYSTEMS AND METHODS

(71) Applicant: Varian Medical Systems, Inc., Palo Alto, CA (US)

(72) Inventors: Flavio Poehlmann-Martins, Fremont, CA (US); Joshua McNeur, Palo Alto, CA (US); Alexander Cahill, San Francisco, CA (US); Ognian Sabev, San Jose, CA (US); Reza Alibazi Behbahani, North Brunswick, NJ (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 392 days.

(21) Appl. No.: 17/482,221

(22) Filed: Sep. 22, 2021

(65) Prior Publication Data

US 2023/0090348 A1 Mar. 23, 2023

(51) Int. Cl.
*A61N 5/10* (2006.01)

(52) U.S. Cl.
CPC ........... *A61N 5/103* (2013.01); *A61N 5/1042* (2013.01)

(58) Field of Classification Search
None
See application file for complete search history.

(56) References Cited

U.S. PATENT DOCUMENTS

| 2011/0206187 | A1* | 8/2011 | Lee | G21K 1/062 |
| | | | | 378/119 |
| 2015/0248942 | A1* | 9/2015 | Bar-David | A61N 5/1042 |
| | | | | 378/145 |
| 2016/0310764 | A1* | 10/2016 | Bharadwaj | A61N 5/1078 |
| 2020/0289851 | A1* | 9/2020 | Dilmanian | A61N 5/1042 |

FOREIGN PATENT DOCUMENTS

DE 102004045330 A1 * 8/2006 ........... A61N 5/1042

\* cited by examiner

*Primary Examiner* — Christine H Matthews
*Assistant Examiner* — Marc D. Honrath
(74) *Attorney, Agent, or Firm* — Harness, Dickey & Pierce, P.L.C.

(57) ABSTRACT

Presented systems and methods enable efficient and effective radiation treatment planning and treatment, including accurate and convenient transmission of the radiation towards a tissue target. In one embodiment, a radiation system includes a particle source, a bremsstrahlung target, and a pinhole collimator. The particle source is configured to produce a particle beam (e.g., an electron beam, etc.). The bremsstrahlung target is configured to receive the particle beam and generate a photon radiation beam. The received particle beam and generated photon radiation beam can correspond to an inflected image. The inflected image can be associated with a tumor/tissue target. The pinhole collimator is configured to receive the photon radiation beam in a pattern that corresponds to the inflected image, invert the photon radiation beam pattern, and forward the results towards a tissue target.

15 Claims, 9 Drawing Sheets

900

910
Generating a particle beam, wherein the particle beam is configured in a pattern that corresponds to an inflected image, wherein the inflected image is associated with a treatment area of a tissue target.

920
Creating a radiation beam based upon the particle beam, wherein the radiation beam configuration corresponds to the inflected image.

930
Inverting the pattern of the radiation beam to create a version of the radiation beam referred to as the treatment radiation beam, wherein the treatment radiation beam corresponds to the treatment area of a tissue target.

940
Forwarding the treatment radiation beam towards the tissue target.

Fig. 9

PINHOLE COLLIMATOR SYSTEMS AND METHODS

BACKGROUND

Radiation therapy is utilized in various medical treatments. Radiation therapy usually involves directing a beam of high energy proton, photon, ion, or electron radiation ("therapeutic radiation") into a tissue target or tissue target volume (e.g., a tissue volume that includes a tumor, lesion, etc.). Typically, before a patient is treated with radiation, a treatment plan specific to that patient is developed. In general, the purpose of the treatment plan is to deliver sufficient radiation to the unhealthy tissue while minimizing exposure of surrounding healthy tissue to the radiation. Traditional radiation systems primarily rely on collimators for directing the radiation to the unhealthy tissue while minimizing exposure of surrounding healthy tissue to the radiation. Conventional approaches to beam collimation can be likened to irradiating a treatment target from a point source and moving a physical barrier to "shade" healthy tissue. As a result, large shields usually need to be placed between the point source and the treatment/tissue target. The shields usually need to be physically moved so that the desired shape can be "projected" onto the tumor/tissue target. The collimators are typically located in a treatment head and a substantial portion of the treatment head size and weight come from the radiation shield and collimation system. Further, a collimation system typically occupies a significant fraction of the source-axis-distance (SAD), which also limits patient clearance and thus treatment options. In addition, conventional multi-leaf collimators (MLC) are relatively slow and provide limited resolution due to finite leaf width.

While the potential benefits from reducing the size and complexity of the treatment head shield and the collimation system can be significant, the realization of this objective has traditionally been very challenging (e.g., not practical, not possible, etc.). Smaller linear accelerators (Linacs), by themselves, do not translate into significantly smaller or lighter treatment heads because the shielding thickness is primarily determined by beam energy, not by the Linac size. In addition, conventional thinking typically included the concept that thinner shields would require the discovery of a new ultra-high Z element (which is not a realistic option).

SUMMARY

Presented systems and methods enable efficient and effective radiation treatment planning and treatment, including accurate and convenient transmission of the radiation towards a tissue target. In one embodiment, a radiation system includes a particle source, a bremsstrahlung target, and a pinhole collimator. The particle source is configured to produce a particle beam (e.g., an electron beam, etc.). The bremsstrahlung target is configured to receive the particle beam and generate a photon radiation beam. The received particle beam and generated photon radiation beam can correspond to an inflected image. The inflected image can be associated with a tumor/tissue target. The pinhole collimator is configured to receive the photon radiation beam in a pattern that corresponds to the inflected image, invert the photon radiation beam pattern, and forward the results towards a tissue target. The inflected image corresponds to an inverted image associated with a cross section of the tissue target.

The pinhole collimator includes a pinhole opening configured to allow the photon radiation beam to pass through the collimator. The pinhole collimator can include conical cavities that direct the photon beam into and out of the pinhole opening. In one exemplary implementation, the pinhole collimator includes a first conical cavity configured to direct the photon beam towards a pinhole opening, and a second conical cavity configured to direct the photon beam away from the pinhole opening, wherein the narrow ends of the conical cavities are coupled to opposite sides of the pinhole opening. The radiation system can include a scanning component configured to scan the inflected image onto the bremsstrahlung target so that the inflected image corresponds to an inflected image of a tissue target cross section. The particle source can include a 2-dimensional (2d) array micro-beam system that generates a particle beam in an inflected image configuration that corresponds to an inflected image of a tissue target cross section. The inflected image can correspond to a scaled inversion of a cross section of a tissue target. The radiation beam can correspond to a precise image of a complex tumor shape.

In one embodiment, a radiation method comprises: generating a particle beam wherein the particle beam is configured in a pattern that corresponds to an inflected image; creating a radiation beam based upon the particle beam, wherein the radiation beam configuration corresponds to the inflected image; inverting the pattern of the radiation beam to create a version of the radiation beam referred to as the treatment radiation beam; and forwarding the treatment radiation beam towards the tissue target. The inflected image can be associated with a treatment area of a tissue target. The treatment radiation beam can correspond to the treatment area of a tissue target. In one embodiment the radiation beam is a photon radiation beam. The radiation beam can be an X-ray radiation beam. The inverting can include directing the radiation beam through a pinhole collimator opening. The method can include optimizing the location of the pinhole collimator opening with respect to a location of the tissue target. In one exemplary implementation, the inflected image corresponds to an inverted image associated with of a cross section of the tissue target. The method can include selecting one of a plurality of pinhole collimator openings and directing the radiation beam through the selected pinhole collimator opening.

In one embodiment, a radiation system includes an accelerator, a bremsstrahlung target, and a collimator system. The accelerator is configured to produce a particle beam (e.g., electron particle beam, etc.). The bremsstrahlung target configured to receive the electron particle beam and generate a photon radiation beam, wherein the received particle beam and generated photon radiation beam correspond to an inflected image. The collimator system is configured to receive the photon radiation beam in a configuration that corresponds to the inflected image, invert the photon radiation beam configuration, and forward the results towards a tissue target. In one embodiment, the collimator system includes a plurality of selectable pinhole collimators. A first one of the plurality of selectable pinhole collimators can be configured differently than a second one of the plurality of selectable pinhole collimators. A selection can be based on a field size. In one exemplary implementation, the collimator system includes a pinhole opening coupled to double conical cavities arranged in an hourglass configuration.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

FIG. 9 is a flow chart of an exemplary method in accordance with an embodiment.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Figure 1:
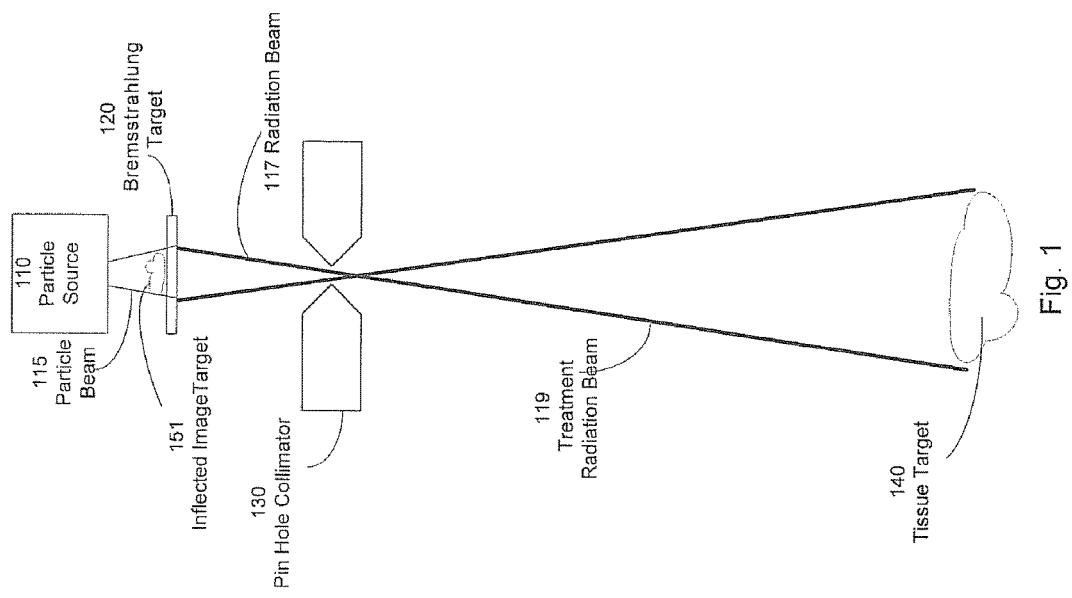
FIG. 1 is a block diagram of an exemplary radiation system in accordance with one embodiment.

FIG. 1 is a block diagram of exemplary radiation system 100 in accordance with one embodiment. Radiation system 100 includes particle source 110, bremsstrahlung target 120, and pin hole collimator 130. The particle source 110 is configured to produce a particle beam 115 (e.g., electron particle beam, proton particle beam, etc.). The bremsstrahlung target 120 is configured to receive the particle beam 115 and generate a photon radiation beam 117, wherein the received particle beam 115 and generated photon radiation beam 117 correspond to an inflected image 151. The inflected image can be associated with a tumor/tissue target. The pinhole collimator 130 is configured to receive the photon radiation beam in a pattern that corresponds to the inflected image, invert the photon beam pattern and forward the resulting treatment radiation beam 119 towards a tissue target 140.

The inflected image can correspond to a cross section of a tissue target. In one embodiment, the inflected image corresponds to an inversion of a cross section of a tissue target. The inflected image can be a scaled inversion of a cross section of a tissue target. In one exemplary implementation, the photon radiation beam corresponds to a precise image of a complex tumor shape of the tissue target.

Figure 2:
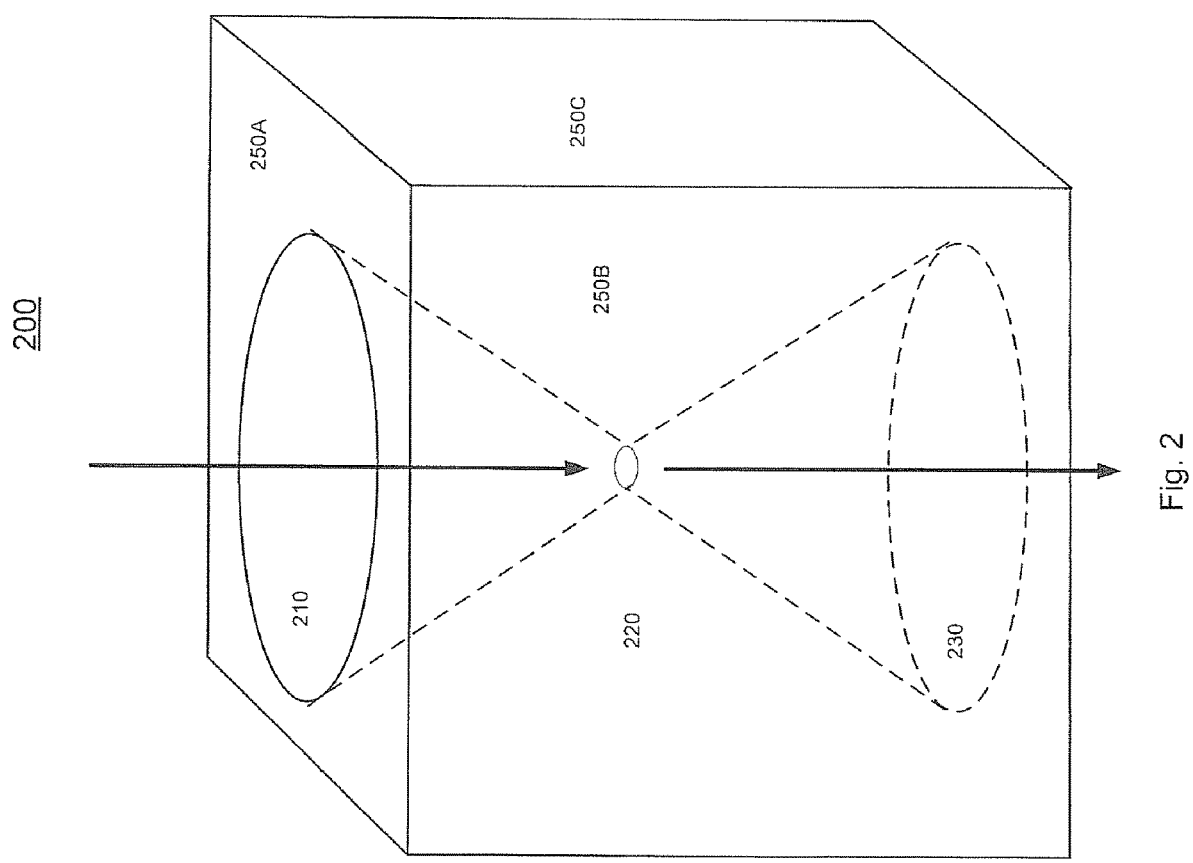
FIG. 2 is a block diagram of an exemplary pinhole collimator in accordance with an embodiment.

FIG. 2 is a block diagram of an exemplary pinhole collimator 200 in accordance with an embodiment. Pinhole collimator 200 includes a conical portion 210 pinhole opening 220 and conical portion 230. Pinole collimator 200 can have solid portions (e.g., 250A, 250B, 250C, etc.). Pinole collimator 200 can have cavity portions (e.g., 210, 220, 230, etc.).

In one embodiment, a pinhole collimator includes a pinhole opening configured to allow a photon beam to pass through. The pinhole collimator can include conical cavities (e.g., 210, 230, etc.) that direct the photon beam into and out of the pinhole opening. The pinhole collimator includes a first conical cavity and a second conical cavity, wherein the narrow ends of the conical cavities are coupled to opposite sides of the pinhole opening. The double conical sections can have an hourglass configuration. The pinhole collimator includes a first conical cavity configured to direct the photon beam towards a pinhole opening and a second conical cavity configured to direct the photon beam away from the pinhole opening.

The pinhole collimator shown in FIG. 2 can be further optimized. The pinhole opening or waist diameter and conical cavity surface angles can be optimized for penumbra and treatment field size. The collimator can take the form of a carousel with different hourglass geometries that can be selected for different desired field sizes. In addition, the locations of the pinhole collimator and target can be further optimized. In one embodiment, the pinhole collimator includes segments with moving shapes to dynamically adjust geometric parameters of the pinhole collimator.

In one embodiment, a pinhole collimator can include 10 cm thick tungsten with an hourglass shaped pinhole. In one exemplary implementation, the waist or pinhole opening of the hourglass has a 2 mm radius.

Figure 3:
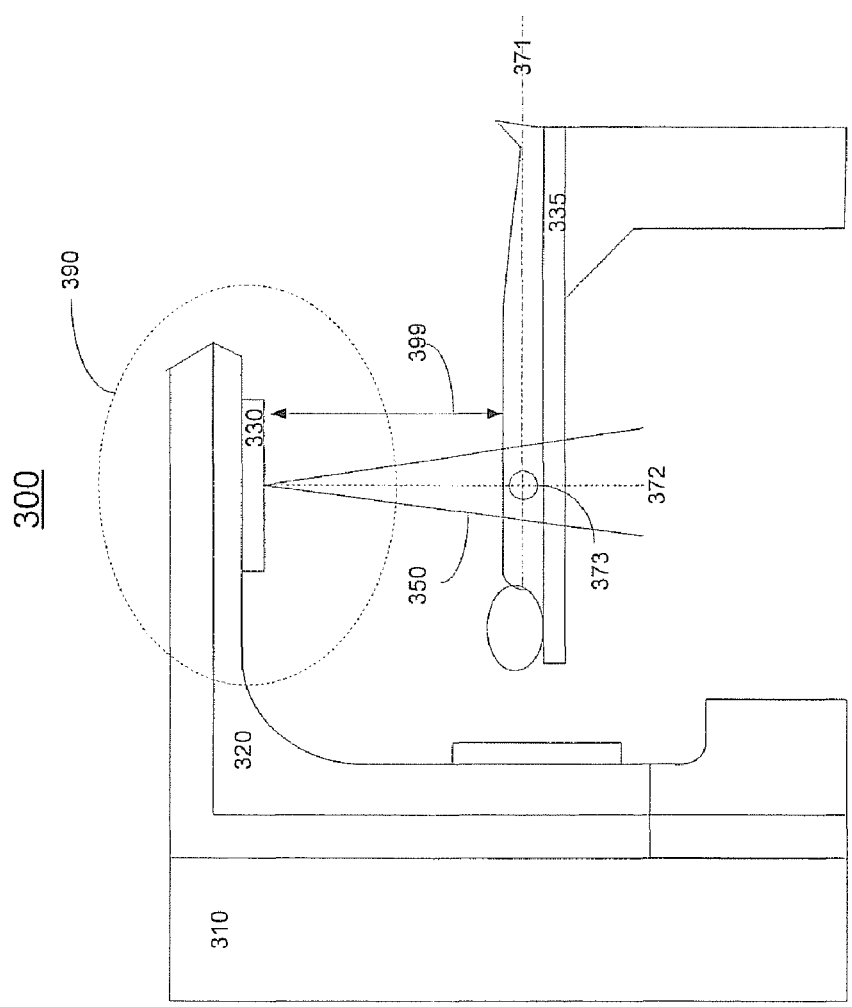
FIG. 3 illustrates a block diagram of an exemplary radiation treatment system in accordance with one embodiment.

FIG. 3 illustrates a block diagram of an exemplary radiation treatment system 300 in accordance with one embodiment. Radiation treatment system 300 may be similar to a Varian TrueBeam® radiotherapy system, commercially available from Varian Medical Systems, Palo Alto, CA.

Stand 310 supports a rotatable gantry 320 with a treatment head 330. The treatment head 330 may extend into the gantry 320. In proximity to stand 310 there is arranged a control unit (not shown) which includes control circuitry for controlling the different modes of operation of the system 300. In one embodiment, treatment head 330 includes a pinhole collimator.

Radiation treatment system 300 comprises a radiation system (e.g., similar to 100 in FIG. 1, etc.), for example, within gantry 320, utilized to create a radiation beam. Typically, radiation treatment system 300 is capable of generating either an electron (particle) beam or an X-ray (photon) beam for use in the radiotherapy treatment of patients on a treatment couch 335. A high voltage source is provided within the stand and/or in the gantry to supply voltage to an electron gun (not shown) positioned on an accelerator guide located in the gantry 320. Electrons are emitted from the electron gun into an accelerator where they are accelerated. A source supplies radio frequency (microwave) power for the generation of an electric field within the waveguide. The electrons emitted from the electron gun are accelerated in the waveguide by the electric field, and exit the waveguide as a high-energy electron beam for example, at megavoltage energies. The electrons impact a bremsstrahlung target and photon radiation is produced. In one embodiment, the gantry includes a component (e.g., bend magnets, etc.) for redirecting the beams (e.g., in the direction of a patient, etc.).

As illustrated in FIG. 3, a patient is shown lying on the treatment couch 335. The radiation beam 350 is emitted from the treatment head 330 (e.g., as described above, etc.) towards the patient. In an x-ray implementation a patient plane 371 is usually positioned about one meter from the X-Ray target, and the rotational axis of the gantry 320 is located on the plane 371, such that the distance between the target and the isocenter 373 remains constant when the gantry 320 is rotated. It is appreciated that for electron FLASH therapy, the patient plane 371 may be less than one meter from the electron source. The isocenter 373 is at the intersection between the patient plane 371 and the central axis 372 of radiation beam 350. A treatment volume to be irradiated may be located about the isocenter 373. It is appreciated that some treatment plans may utilize a primary target that is off of the central beam axis, and such arrangements are within the scope of embodiments in accordance with the present invention.

Figure 4:
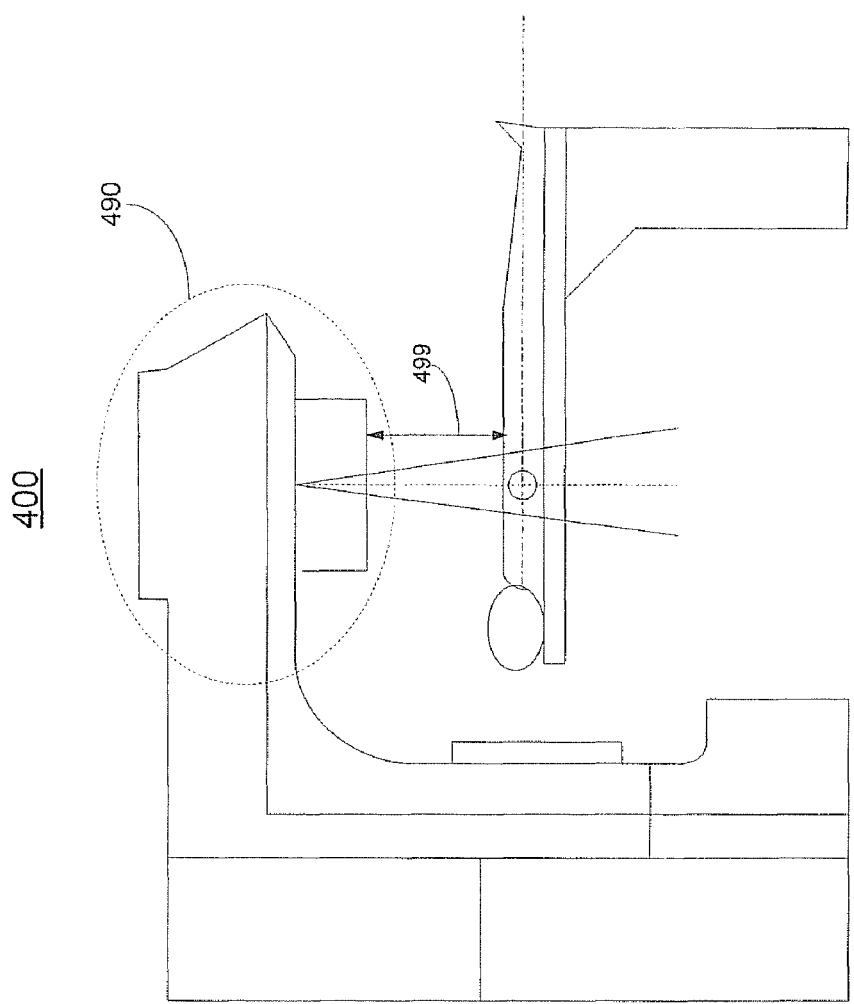
FIG. 4 is a block diagram of an exemplary traditional system.
Figure 5:
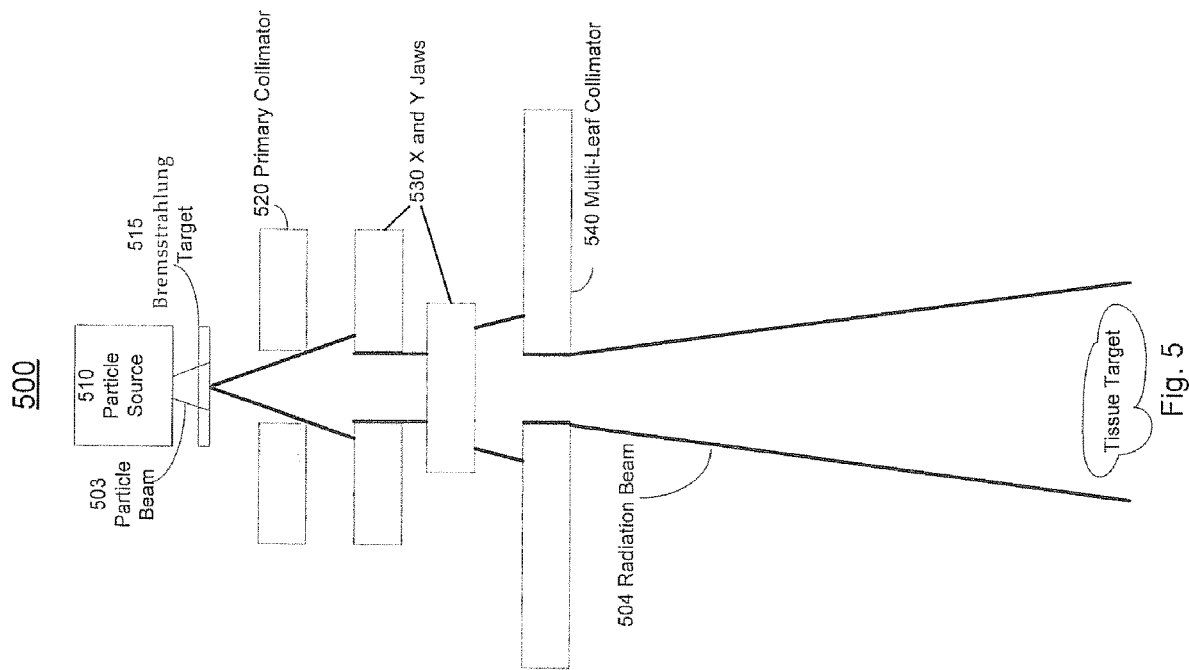
FIG. 5 illustrates a block diagram of an exemplary beam path within a traditional radiation treatment system.

FIG. 4 is a block diagram of an exemplary traditional system 400. It is appreciated the head and gantry portion 390 of novel pinhole gantry radiation system 300 is significantly smaller and lighter than the head and gantry portion 490 of system 400, and the clearance 399 is significantly larger than the clearance 499. Similarly, the SAD of novel pinhole gantry radiation system 300 is also significantly greater than traditional system 400. The traditional head and gantry is usually larger and heavier because a traditional system typically has many more components and shielding in the beam path than a novel pinhole collimator radiation system. FIG. 5 illustrates a block diagram of an exemplary beam path 500 within a traditional radiation treatment system 400. It is appreciated that the illustrated components of beam path 500 are exemplary. Additional components (e.g., a flattening filter (not shown), etc.) may also be included. A particle source 510 generates an electron beam 503 that impacts bremsstrahlung target 515 producing a radiation beam 504. The radiation beam 504 passes through primary collimator 520, X and Y jaws 530, and multi-leaf collimator 540 which are positioned in the head portion 490 (FIG. 4). The primary collimator 520, X and Y jaws 530, and multi-leaf collimator 540 take up considerable space and typically have a significant weight.

With reference back to pinhole collimator embodiments, a pinhole collimator design can include "painting" an inverse and scaled image of the tumor onto the bremsstrahlung target. A pinhole collimator system can create an inflected image of the tissue target. In the case of electron treatment modes, the inverse shape can be painted onto a scattering foil. There are various ways of creating the inflected image, and the pinhole collimation is compatible with each. In one embodiment, a scanning component is utilized to paint the inflection image.

Figure 6:
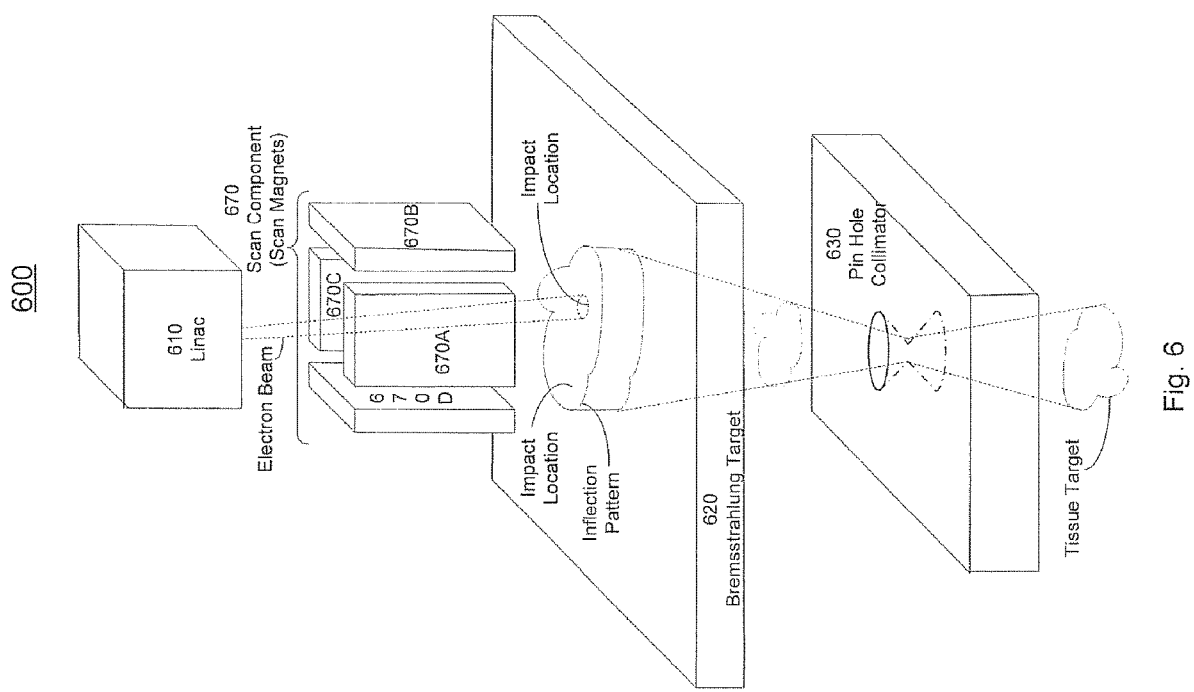
FIG. 6 is a block diagram of an exemplary radiation system with a scanning component in accordance with an embodiment.

FIG. 6 is a block diagram of exemplary radiation system 600 in accordance with an embodiment. Radiation system 600 includes particle source 610, bremsstrahlung target 620, pin hole collimator 630, and scanning component 670 (e.g., including scan magnets 670A, 670B, 670C, and 670D, etc.). In one exemplary implementation, the particle source 610 is a Linac. The scanning component is configured to direct and control the electron particle beam to "paint" the inflected image or pattern. The scanning component can scan in a horizontal and a vertical direction independently.

The inflection image/pattern can be created by steering the electron beam that is produced by the Linac 610 onto the bremsstrahlung target to create the intended shape. In one embodiment, Helmholtz coils (indicated as scanning magnets in FIG. 6) can generate magnetic fields that raster scan the charged electron beam across the target plane. In one exemplary implementation, off the shelf coil setups can be utilized (e.g., possibly with magnetic yokes, etc.) to generate magnetic fields sufficient to steer even the highest energy electron beams generated by medical linacs (e.g., typically on the scale of tens of MeV). An optional beam position monitor (not shown) can provide closed-loop control of the beam location.

Figure 7:
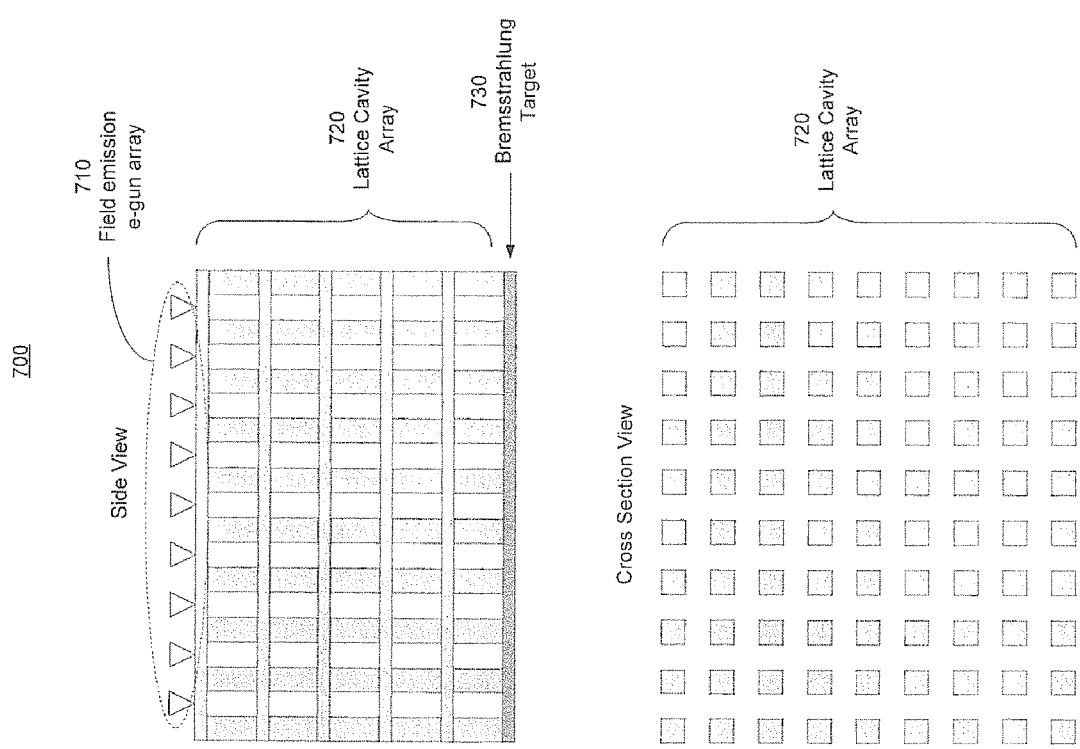
FIG. 7 is a block diagram of an exemplary 2d array of micro-beams in accordance with one embodiment.

FIG. 7 is a block diagram of exemplary 2 dimensional (2d) array micro-beam system 700 in accordance with one embodiment. In one exemplary implementation, 2 dimensional (2d) array micro-beam system includes a 2d array of micro-linacs be coupled with a 2d field emission electron cathode array. The 2d array of micro-beams 700 includes field emission array 710, lattice cavity array 720, and bremsstrahlung target 730. The 2d array of micro-beams 700 can include a pixelated micro-linac array and a field emission electron cathode array. The micro-linac array includes dielectric based structures that are powered by lasers. The micro-linac array includes metallic structures that are powered by a THz source. Thus, the output of micro-linacs in a 2d array is compatible with the proposed imaging/scanning scheme for a pinhole collimator system.

In one embodiment, a pinhole collimator can be optimized to achieve a combination of the following characteristics. Radically increased collimation speed through the elimination of moving parts (this can be particularly relevant to Photon FLASH approaches). Cost reduction through the elimination of traditional components such as MLCs, jaws, some shielding, and so on (this can be particularly relevant to multi-linac Photon FLASH systems). Improved patient clearance due to significant reduction in thickness of the collimation system. Smaller collimation systems can be particularly relevant to scenarios where it is desirable to reduce SAD for higher dose rates (e.g., FLASH, etc.). Smaller collimation systems can also be relevant to ring type gantries where larger ring diameters mean better patient comfort or to C-arm gantries where more clearance enables better solid angles for noncoplanar treatments. New treatment modalities are possible as pinhole collimation can project shapes that cannot typically be created with moving MLC leaves. In one embodiment, a pinhole collimation system eliminates the need for any physical motion of collimator components to achieve a radiation treatment image/projection. In addition, pinhole collimator systems enable improved resolution as resolution is no longer limited by leaf thickness of the MLC. In one exemplary implementation, a pinhole collimator system can generate any beam profile, including concave shapes, hollow shapes, and so on. High power levels on target are also available since the beam can be scanned across the bremsstrahlung target, distributing the thermal power deposition over a larger area.

Figure 8:
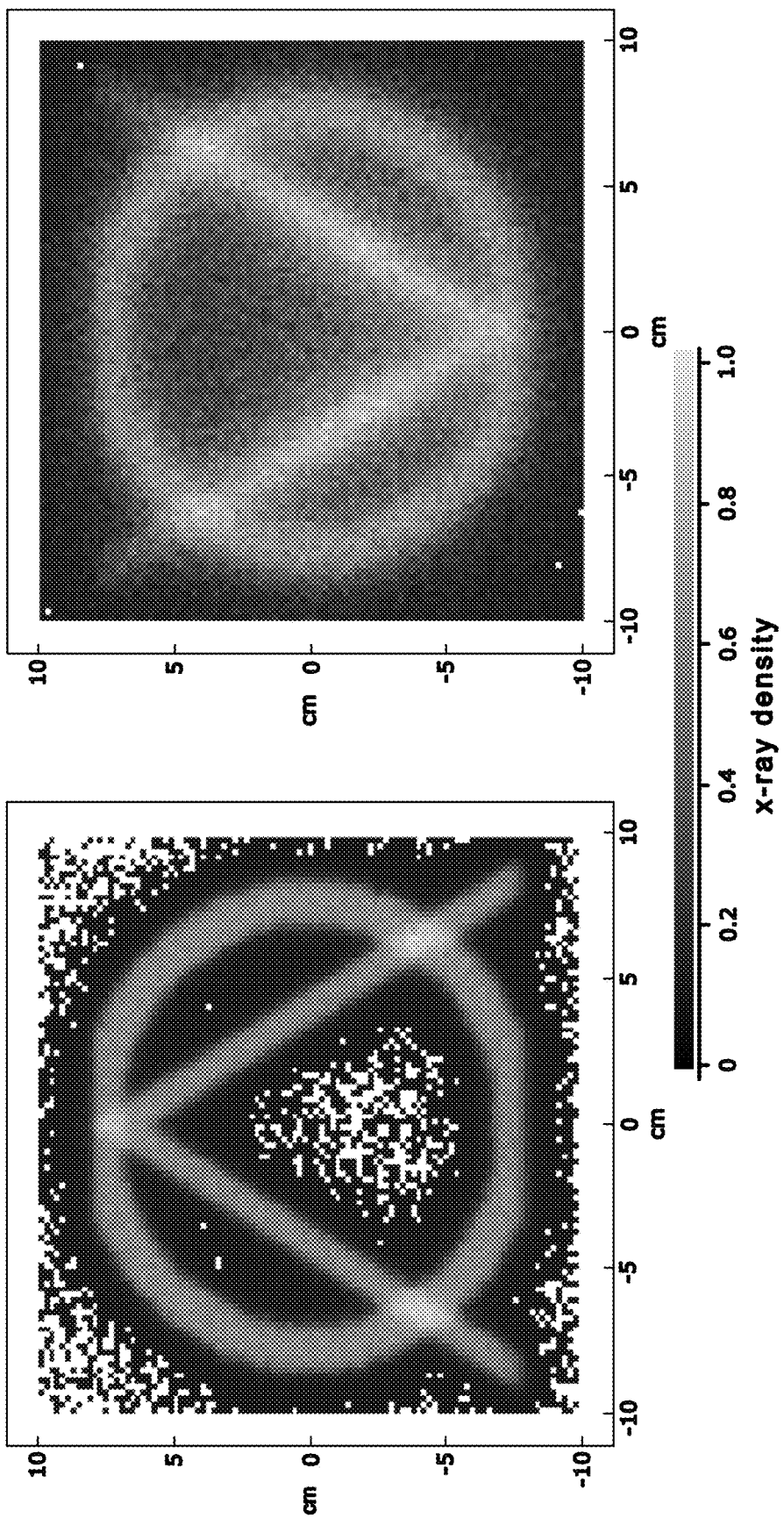
FIG. 8 shows exemplary results of a preliminary Monte Carlo simulation that compares the X-rays generated at the bremsstrahlung target to an x-ray beam profile projected onto a tumor.

FIG. 8 shows exemplary results of a preliminary Monte Carlo simulation that compares the X-rays generated at the target (left) to the X-ray beam profile projected onto the tumor (right). Further it can be seen that profile shapes can be projected onto the tumor/tissue target that are usually impossible to achieve with conventional MLC collimation systems. In one embodiment, the Monte Carlo simulations send X-rays through a 2 mm radius pinhole in 10 cm deep tungsten. The left image shows X-rays coming off the electron target. The right image shows the X-rays on a plane 40 cm downstream. The scale bar denotes X-ray density.

FIG. 9 is a flow chart of an exemplary method in accordance with an embodiment.

In block 910, a particle beam is generated, wherein the particle beam is configured in a pattern that corresponds to an inflected image, wherein the inflected image is associated with a treatment area of a tissue target.

In block 920, a radiation beam is created based upon the particle beam, wherein the radiation beam configuration corresponds to the inflected image. In one embodiment, the radiation beam is an X-ray photon radiation beam.

In block 930, the pattern of the radiation beam is inverted to create a version of the radiation beam referred to as the treatment radiation beam, wherein the treatment radiation beam corresponds to the treatment area of a tissue target.

In block 940, the treatment radiation beam is forwarded towards the tissue target.

The method can further comprise optimizing the location of the pinhole collimator opening with respect to a location of the tissue target. The inverting can include directing the radiation beam through a pinhole collimator opening. The method can further comprise selecting one of a plurality of pinhole collimator openings and directing the radiation beam through the selected pinhole collimator opening.

Some portions of the detailed descriptions are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. Portions of the detailed description that follows are presented and discussed in terms of methods. Although steps and sequencing thereof are disclosed in figures herein describing the operations of those methods, such steps and sequencing are examples only. Embodiments are well suited to performing various other steps or variations of the steps recited in the flowcharts of the figures herein, and in a sequence other than that depicted and described herein.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "representing," "applying," "indicating," "storing," "using," "adjusting," "including," "computing," "displaying," "associating," "rendering," "determining," or the like, refer to actions and processes of a computer system or similar electronic computing device or processor. The computer system or similar electronic computing device manipulates and transforms data represented as physical (electronic) quantities within the computer system memories, registers or other such information storage, transmission or display devices. Terms such as "dose" or "dose rate" or "fluence" generally refer to a dose value or dose rate value or fluence value, respectively; the use of such terms will be clear from the context of the surrounding discussion.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Computer storage media includes volatile and nonvolatile, removable and non-removable media implemented in any method or technology for storage of information such as computer-readable instructions, data structures, program modules or other data. Communication media can embody computer-executable instructions, data structures, and program modules, and includes any information delivery media.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation system comprising:
a particle source configured to produce an electron particle beam;
a bremsstrahlung target configured to receive the electron particle beam and generate a photon radiation beam, wherein the electron particle beam and the photon radiation beam are configured in a pattern corresponding to an inflected image, the inflected image being a scaled inversion of a cross section of a target tissue; and
a pinhole collimator configured to receive the photon radiation beam in the pattern that corresponds to the inflected image, invert the pattern of the photon radiation beam, and forward the photon radiation beam with the inverted pattern towards the target tissue.

2. The radiation system of claim 1, wherein the pinhole collimator includes a pinhole opening configured to allow the photon radiation beam to pass through the pinhole collimator.

3. The radiation system of claim 2, wherein the pinhole collimator includes conical cavities that direct the photon radiation beam into and out of the pinhole opening.

4. The radiation system of claim 1, wherein the pinhole collimator includes a first conical cavity configured to direct the photon radiation beam towards a pinhole opening, and a second conical cavity configured to direct the photon radiation beam away from the pinhole opening, wherein the first conical cavity and the second conical cavity are coupled to create the pinhole opening.

5. The radiation system of claim 1, further comprising one or more scan magnets configured to scan the inflected image onto the bremsstrahlung target so that the inflected image corresponds to an inflected image of the cross section of the target tissue.

6. The radiation system of claim 1, wherein the particle source includes a 2-dimensional (2D) array micro-beam system that generates the electron particle beam in an inflected image configuration that corresponds to the inflected image of the cross section of the target tissue.

7. The radiation system of claim 1, wherein the photon radiation beam corresponds to an image of a tumor shape.

8. A radiation method comprising:
generating a particle beam, wherein the particle beam is configured in a pattern that corresponds to an inflected image, wherein the inflected image is associated with a treatment area of a target tissue;

creating a radiation beam from the particle beam, wherein a configuration of the radiation beam corresponds to the inflected image;

inverting a pattern of the radiation beam to create treatment radiation beam by directing the radiation beam through a pinhole collimator opening, wherein the treatment radiation beam corresponds to the treatment area of the target tissue; and forwarding the treatment radiation beam towards the target tissue.

9. The radiation method of claim 8, further comprising optimizing a location of the pinhole collimator opening with respect to a location of the target tissue.

10. The radiation method of claim 8, wherein the inflected image corresponds to an inverted image associated with a cross section of the target tissue.

11. The radiation method of claim 8, wherein the pinhole collimator opening is selected from a plurality of pinhole collimator openings.

12. A radiation system comprising:

an accelerator configured to produce a particle beam;

a bremsstrahlung target configured to receive the particle beam and generate a photon radiation beam, wherein the particle beam and the photon radiation beam correspond to an inflected image; and a collimator system including a plurality of selectable pinhole collimators, the collimator system configured to receive the photon radiation beam in a configuration that corresponds to the inflected image, invert the configuration of the photon radiation beam, and forward the photon radiation beam with the inverted configuration towards a target tissue.

13. The radiation system of claim 12, wherein a first of the plurality of selectable pinhole collimators is configured in a first orientation and a second of the plurality of selectable pinhole collimators is configured in a second orientation, the first orientation being different than the second orientation.

14. The radiation system of claim 12, wherein a selection of one of the plurality of selectable pinhole collimators is based on an intended field size.

15. The radiation system of claim 12, wherein the collimator system includes a pinhole opening formed at an intersection of a first conical cavity and a second conical cavity arranged in an hourglass configuration.

* * * * *